United States Patent [19]
Ryles et al.

[11] Patent Number: 5,902,568
[45] Date of Patent: May 11, 1999

[54] METHOD FOR WHITENING TEETH

[75] Inventors: Christine Watson Ryles, Milford; Stephen Roy Barrow, Trumbull; David Robert Williams, Monroe, all of Conn.

[73] Assignee: Chesebrough-Pond's USA Co., Division of Conopco, Inc., Greenwich, Conn.

[21] Appl. No.: 08/979,645

[22] Filed: Nov. 26, 1997

Related U.S. Application Data

[63] Continuation-in-part of application No. 08/783,972, Jan. 15, 1997, abandoned.

[51] Int. Cl.⁶ .............................. A61K 7/16; A61K 7/20; A61K 33/40
[52] U.S. Cl. .............................. 424/53; 424/49; 424/613; 424/616; 424/717
[58] Field of Search ............................................ 424/49–88

[56] References Cited

U.S. PATENT DOCUMENTS

| | | |
|---|---|---|
| D. 315,496 | 3/1991 | Pettengill . |
| 2,826,339 | 3/1958 | Maillard . |
| 3,166,221 | 1/1965 | Nielsen . |
| 3,935,304 | 1/1976 | Januszewski et al. . |
| 3,935,305 | 1/1976 | Delaney et al. . |
| 3,952,920 | 4/1976 | Bergman . |
| 3,988,433 | 10/1976 | Benedict . |
| 4,046,288 | 9/1977 | Bergman . |
| 4,121,739 | 10/1978 | Devaney et al. . |
| 4,240,566 | 12/1980 | Bergman . |
| 4,301,948 | 11/1981 | Czech et al. . |
| 4,528,180 | 7/1985 | Schaeffer . |
| 4,687,663 | 8/1987 | Schaeffer . |
| 4,721,614 | 1/1988 | Winston et al. . |
| 4,742,940 | 5/1988 | Wilkinson . |
| 4,849,213 | 7/1989 | Schaeffer . |
| 4,976,955 | 12/1990 | Libin . |
| 5,020,694 | 6/1991 | Pettengill . |
| 5,038,963 | 8/1991 | Pettengill et al. . |
| 5,098,303 | 3/1992 | Fischer . |
| 5,122,365 | 6/1992 | Murayama . |
| 5,171,564 | 12/1992 | Nathoo et al. . |
| 5,208,010 | 5/1993 | Thaler . |
| 5,240,415 | 8/1993 | Haynie . |
| 5,256,402 | 10/1993 | Prencipe et al. . |
| 5,290,566 | 3/1994 | Schow et al. . |
| 5,401,495 | 3/1995 | Murayama . |
| 5,631,000 | 5/1997 | Pellico et al. . |
| 5,645,428 | 7/1997 | Yarborough . |

FOREIGN PATENT DOCUMENTS

| | | |
|---|---|---|
| 0 388 185 | 9/1990 | European Pat. Off. . |
| 2 290 234 | 12/1995 | United Kingdom . |
| 88/06879 | 9/1988 | WIPO . |
| 95/09603 | 4/1995 | WIPO . |
| 96/28133 | 9/1996 | WIPO . |
| 97/11676 | 4/1997 | WIPO . |
| 97/21419 | 6/1997 | WIPO . |

OTHER PUBLICATIONS

Colgate Baking Soda & Peroxide Carton –1996.

*Primary Examiner*—Shep K. Rose
*Attorney, Agent, or Firm*—Milton L. Honig

[57] ABSTRACT

A method for whitening teeth is provided which involves applying to the teeth a mixture of a peroxide and a bicarbonate salt. Advantageously, the peroxide and bicarbonate salt are stored as active ingredients in separate respective compositions of a dispensing container. Preferably the dispensing container is a pump in the form of an upper and lower body telescopically engageable one with another, the upper body including at least two hollow and separate parallel cylinders each containing one of the compositions. These compositions may then be dispensed through relative compression of the pistons within the cylinders.

8 Claims, 1 Drawing Sheet

FIG.
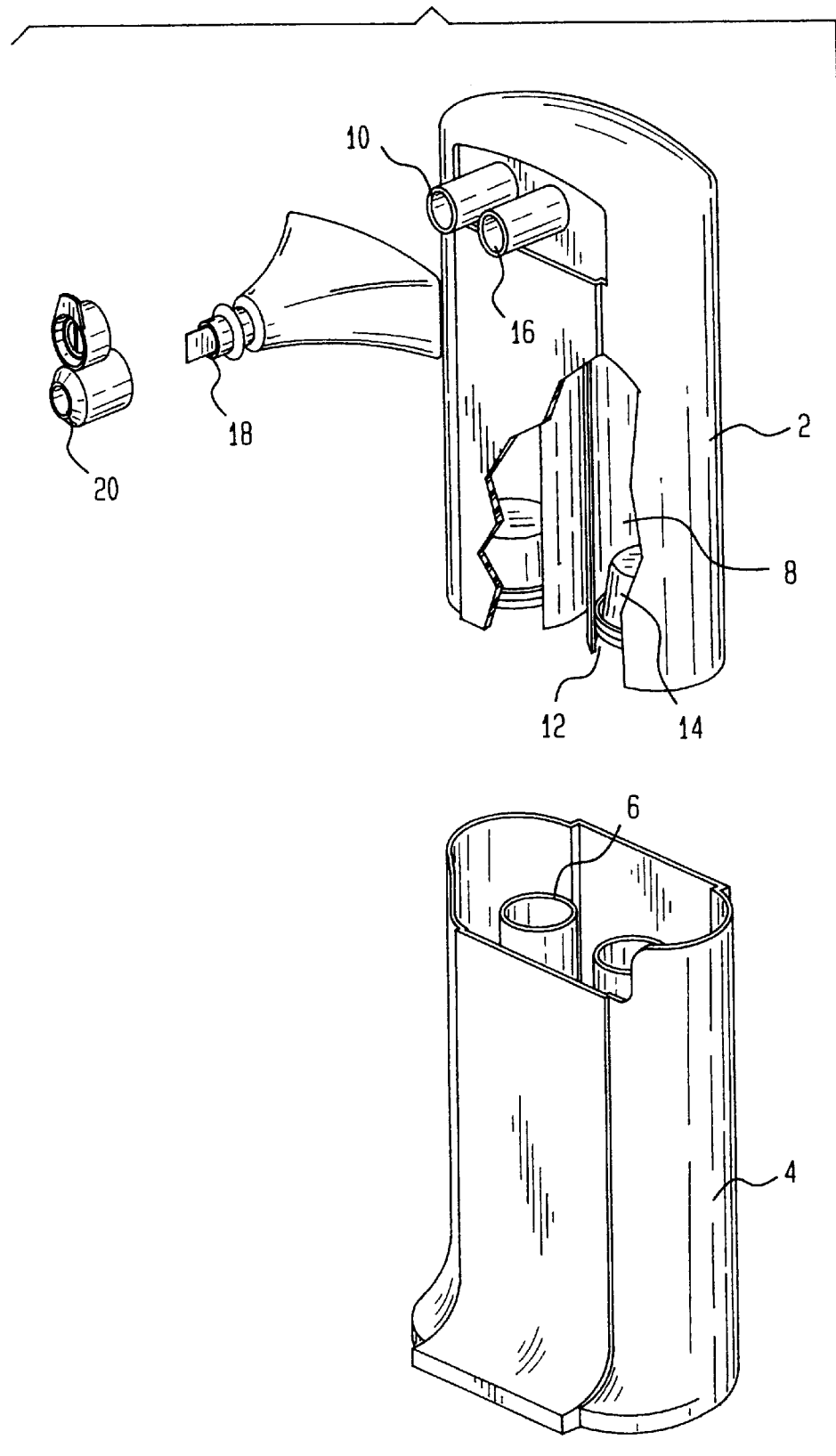

5,902,568

METHOD FOR WHITENING TEETH

This application is a continuation in part of application Ser. No. 08/783,972 filed Jan. 15, 1997, now abandoned.

BACKGROUND OF THE INVENTION

1. Field of the Invention

The invention concerns a method for whitening teeth which removes stain and leaves surfaces brighter.

2. The Related Art

People to some extent are judged by their smile. It is little wonder then that people are concerned with the appearance of their teeth. Stained ugly surfaces detract from the warmth intended to be conveyed by the smile. Stains arise from certain foods, tartar buildup, side effects of medicine and most especially smoking.

Abrasives in dentifrices are a first line of defense in combatting stains. Usually they deliver adequate but not superlative performance. An additional drawback is that abrasives, especially in higher concentrations, may damage enamel. Certain types of stains like those arising from smoking are often not removed by abrasive action alone.

Peroxides have been suggested as whitening agents. Unless employed at relatively high levels and in the presence of a catalyst, the peroxides are only modestly efficient in bleaching enamel.

Oral compositions with peroxide and baking soda (i.e. sodium bicarbonate) have become commercially quite popular. The combination of actives has been reported to promote healthy gums. When in contact, peroxide and baking soda are reactive towards one another. Therefore these ingredients must be maintained separately until time of use. Dispensing packages have been developed which physically isolate peroxide and baking soda by separating them into different compartments. This approach has been described in a series of patents to Schaeffer including U.S. Pat. No. 4,849,213, U.S. Pat. No. 4,528,180 and U.S. Pat. No. 4,687,663. Products based on this technology have been commercially sold in the United States under the Mentadent® brand of Peroxide and Baking Soda toothpastes. Mentadent® has been promoted for its gum care and antitartar properties. Hitherto there had been no indication that this product had any special effectiveness in whitening teeth. Variants of the Mentadent® brand toothpaste ranged in pH from about 7.5 to about 8.5 for a mixture of equal volume streams peroxide and baking soda.

It is an object of the present invention to provide a method for treating teeth to enhance their whiteness.

Another object of the present invention is to provide a method for whitening teeth which achieves its affect more rapidly than other previously known procedures.

Still another object of the present invention is to provide a method for whitening teeth employing relatively low levels of water-insoluble abrasives.

These and other objects of the present invention will become more readily apparent from consideration of the following summary and detailed discussion.

SUMMARY OF THE INVENTION

A method for whitening teeth is provided which includes:
(i) providing an oral composition which includes a first and second composition each of which is stored separate from one another prior to time of use, the first composition containing from 0.01 to 20% of a peroxide by weight of the oral composition, and the second composition containing from 0.05 to 60% of a bicarbonate salt by weight of the oral composition, and the oral composition having a pH from 9.0 to 12;
(ii) dispensing the first and second compositions onto a toothbrush;
(iii) applying the first and second compositions from toothbrush to the teeth;
(iv) brushing the teeth thereby mixing first and second compositions together; and
(v) repeating steps (ii) through (iv) on a plurality of days.

A preferred method of storage and dispensing involves use of a dual compartment dispensing container in the form of a pump. The dispensing container preferably is structured with an upper and lower body telescopically engageable one with another, the upper body including at least two hollow and separate parallel cylinders containing the respective first and second compositions.

BRIEF DESCRIPTION OF THE DRAWINGS

The above features, advantages and objects of the present invention will more fully be appreciated through the following detailed discussion, reference being made to the drawing consisting of a single FIGURE which is an expanded view of a telescopically arranged multi-cavity dispensing pump.

DETAILED DESCRIPTION

Now it has been discovered that teeth may be efficiently whitened by applying thereto a mixture of hydrogen peroxide and sodium bicarbonate. Furthermore it has been found that relatively high pH substantially increases the whitening effect. In particular, it has been found highly effective to employ a pH range from 9.0 to 12, particularly from 9.5 to 10.5 for the total oral composition as measured on a mixed equal volume of the peroxide and the bicarbonate containing streams. Each of the peroxide and bicarbonate actives are incorporated into compositions held separate from one another until just prior to use. Particularly useful is a storage and delivery system utilizing a dispensing pump container having two separate compartments. When the compositions are in the form of semisolids (i.e. a toothpaste), the dispensing container is of the type shown in the Figure.

The dispensing container includes an upper body 2 and a lower body 4, the former telescopically engaging within the latter. Within the lower body 4 are a pair of parallel piston rods 6 rigidly standing, and preferably unitarily molded with the lower body. These rods may be hollow or solid. While the depicted configuration is round, the rods may be rectangular or of any other polygonal shape.

Upper body 2 includes a pair of separate parallel cylinders 8 each having a first generally closed end 10 and a second end 12 telescopically and slidingly accommodating piston heads 14. These heads conform to ride sealingly along interior walls of the cylinders so as to force flowable materials to flow towards the first end of the cylinder. The cylinder walls may be formed as part of the upper body or may be formed as refill cartridges separate and removable from the upper body. Activation of flow is accomplished by hand pressure downward on the top of the upper body which pressure forces the upper body to telescopically descend within the lower body. Movement of the bodies causes pistons 6 to press against each of the respective piston heads 14 moving them upward along respective cylinders 8. Flowable material in each of the cylinders is then forced through a pair of outlet channels 16. Flowable toothpaste exits the outlet channels passing in unmixed streams through an outlet nozzle having a septum 18 maintaining respective toothpastes in unmixed relationship to outlet openings 20.

First and second semi-solid extrudable streams of dentifrice will be stored in each of the respective cylinders 8. The first of the streams will include a peroxide. The peroxide should be capable of generating hydrogen peroxide such as sodium perborate, persilicate, percarbonate, perphosphate, calcium peroxide, sodium peroxide and hydrogen peroxide. Most preferred is an aqueous solution of hydrogen peroxide or an adduct such as urea peroxide. Amounts of the peroxide may range from 0.01 to 20%, preferably from 0.5 to 10%, optimally from 1 to 5% by weight of the total oral composition.

The peroxide containing composition may either be a liquid, paste or gel, preferably the latter. When a gel, water will be present in amounts ranging from 5 to 70%, preferably from 10 to 55%, optimally between 20 to 40% by weight of the first composition.

For anti-caries protection, a source of fluoride ion will normally be present in one or both of the first and second compositions of the total oral composition. Fluoride sources include sodium fluoride, potassium fluoride, stannous fluoride, stannous monofluorophosphate and sodium monofluorophosphate. These sources should release anywhere from 25 to 3500 ppm of fluoride ion. The anti-caries agent will be present in an amount from 0.05 to 3% by weight, preferably from 0.2 to 0.6% by weight of the total oral composition.

A variety of other ingredients normally present in dentifrices can be selected for the peroxide and bicarbonate compositions of the present invention. When the peroxide composition is intended as a gel, it is usual to employ with the water a thickening agent that is a cross-linked acrylic polymer. Alternatively and most preferably, gels can be structured with a polyoxyethylene-polyoxypropylene copolymer. Commercially, copolymers are available from the BASF Corporation under the trademark Pluronic F88, F99, F108 and F127. Most preferred is Pluronic F127 (more commonly described by its CTFA name, Poloxamer 407) which has a molecular weight ranging from 10,000 to 15,000, and containing 70% of the hydrophilic polyoxyethylene moiety. Amounts of the copolymer can range anywhere from 18–25% by weight, preferably between 19 and 24%, by weight of the peroxide containing stream. Poloxamers are particularly suitable for this invention because of their wide pH tolerance, high compatibility with hydrogen peroxide and unique gel properties.

Advantageously, glycerol may also be present in the peroxide composition in an amount from 15 to 60%, preferably in an amount greater than 30% but less than 50%, optimally between 35 to 45% by weight of the peroxide containing stream.

A low pH, preferably a pH no higher than 6, optimally less than 5.0, is maintained for peroxide gels. Acidification is best accomplished through use of a phosphorus-based inorganic or organic acid. Where Carbomer is used as a gel structurant, pH can be as high as 7.5.

The second composition of the oral compositions of the invention will be a bicarbonate-containing composition , preferably an opaque paste. Advantageously, the bicarbonate will be the salt of an alkali metal such as sodium or potassium. Normally, the bicarbonate is included in the composition in an amount sufficient to provide a neutral or basic pH when the total oral composition is contacted with water. Bicarbonate optimally in combination with other alkaline materials such as sodium carbonate can be present in amounts to preferably achieve a pH of from 8.0 to 12, most preferably 8.5 to 11, optimally 9.0 to 11 for the bicarbonate containing stream i.e. the second composition. Typically, the concentration will range from 0.05 to 60%, preferably from 1 to 40%, optimally between 3 and 30% by weight of the second composition.

A humectant and water system will normally be included. Humectants are usually polyols which, for example, may include glycerol, sorbitol, propylene glycol, lactitol, xylitol, polypropylene glycol, polyethylene glycol, hydrogenated corn syrup and mixtures thereof. Generally the amount of humectant will range from 25 to 90%, preferably from 40 to 70% by weight of the first or second semi-solid material. Particularly preferred is a liquid mixture of 3 to 30% water, 0 to 80% glycerol and/or 20 to 80% sorbitol.

A natural or synthetic thickening agent may be present in an amount from 0.1 to 10%, preferably 0.5 to 5% by weight of the second composition. Thickeners may include hydroxypropyl methylcellulose, hydroxyethyl cellulose, sodium carboxymethyl cellulose, xanthan gum, tragacanth gum, karaya gum, arabic gums, Irish moss, starch, alginates and carrageenans.

Surfactants are normally also included in the compositions, especially in the bicarbonate compositions of this invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from 0.5 to 5% by weight of a respective first or second composition.

Anti-tartar agents may also be included. Most suitable are polyphosphate salts, especially tripolyphosphate and pyrophosphates. Counterions for these phosphates may be the alkali metal, alkaline earth metal, ammonium, $C_2$—$C_6$ alkanolammonium and salt mixtures thereof. Representative of polyphosphates are sodium tripolyphosphate, sodium hexametaphosphate, potassium hydrogen phosphate, sodium hydrogen phosphate, disodium pyrophosphate, dipotassium pyrophosphate, tetrasodium pyrophosphate, tetrapotassium pyrophosphate and mixtures of these salts. Amounts of the polyphosphate may range from 0.5 to 20%, preferably from 1 to 8%, optimally from 1.2 to 4.5% by weight of the oral composition. As an alternative to phosphates, zinc salts may be utilized as anti-tartar agents. Most preferred is zinc citrate trihydrate. Amounts of the zinc salt may range from 0.5 to 20%, preferably from 1 to 8%, optimally from 2 to 6% by weight of the oral composition.

An abrasive in addition to the bicarbonate will normally be included in the second composition. Abrasives may be selected from water-insoluble alkali or alkaline earth metal salts of carbonate, aluminate and silicate. Especially preferred are silica, and alumina. Amounts of the abrasive will range from 5 to 80%, preferably from 10 to 30% by weight of the oral composition.

Sweetening agents such as saccharin, sodium cyclamate, aspartame, sucrose and the like may be included at levels from 0.1 to 5% by weight of the oral composition.

Other additives may also be incorporated into the oral compositions including preservatives, silicones, other synthetic or natural polymers such as Gantrez S-97, and anti-gingivitis active. Pigments such as titanium dioxide may also be incorporated for their opacifying effect at levels which may range from 0.01 to 1%, preferably from 0.1 to 0.5%, optimally from 0.15 to 0.2% by weight of the total oral composition. The amounts and particle size or morphology of titanium dioxide should not interfere either to enhance or detract from the whitening effect of the peroxide/bicarbonate interaction.

In the method of the present invention, the first and second compositions with respective peroxide and bicarbonate components are dispensed in approximately equal volume onto a bristle head of a toothbrush. The toothbrush head with the compositions is then applied to the teeth where the first and second compositions are mixed together during brushing action. A certain level of whitening is achieved in the first application but the procedure is intended for repeated use on a plurality of days. Each exposure on the teeth should last anywhere from 10 seconds to 5 minutes, preferably from 30 seconds to 3 minutes, and optimally about 2 minutes per brushing. Advantageously there are two brushings per day. Best effectiveness is achieved when the number of days brushing are at least 7, preferably 15 days and optimally at least 30 days.

The following examples will more fully illustrate the embodiments of this invention. All parts, percentages and proportions referred to herein and in the appended claims are by weight of the total composition unless otherwise stated. Except in the examples, or where otherwise explicitly indicated, all numbers in this description indicating amounts of material or conditions are to be understood as modified by the term "about".

EXAMPLE 1

Typical of whitening paste and gel compositions of the present invention are those detailed under Tables I and II.

TABLE I

Bicarbonate Paste Composition

| INGREDIENT | WT. % |
|---|---|
| Polyol II (sorbitol and other sugars) | 33.60 |
| Syloid 63XX (abrasive silica) | 30.00 |
| Sodium Bicarbonate | 10.00 |
| PEG 32 (polyethylene glycol) | 5.00 |
| Sylox 15x (thickening silica) | 2.00 |
| Flavor | 1.00 |
| Sodium Lauryl Sulfate | 2.98 |
| SD Alcohol 38B | 2.84 |
| Cellulose Gum | 0.80 |
| Sodium Saccharin | 0.54 |
| Menthol | 0.50 |
| Sodium Fluoride | 0.44 |
| Titanium Dioxide | 0.30 |
| Deionized Water | Balance |

TABLE II

Peroxide Gel Composition

| COMPONENT | WT. % |
|---|---|
| Glycerin | 40.00 |
| Pluronic F127 | 20.00 |
| Hydrogen Peroxide (35% food grade) | 4.285 |
| Zinc Citrate Trihydrate | 4.00 |
| FD&C Blue | 0.005 |
| Phosphoric Acid (85% w/w) | 0.15 |
| Deionized Water | Balance |

EXAMPLE 2

Another set of compositions suitable for the present invention are the paste and gel formulations detailed under Tables III and IV.

TABLE III

Bicarbonate Paste Composition

| COMPONENT | WT. % |
|---|---|
| Sorbitol | 30.80 |
| Syloid 63XX (abrasive silica) | 20.00 |
| Sodium Bicarbonate | 15.00 |
| Sodium Carbonate | 5.00 |
| PEG 32 (polyethylene glycol) | 5.00 |
| Sodium Pentaphosphate | 4.00 |
| Sodium Tetrapyrophosphate | 3.00 |
| Sodium Lauryl Sulfate | 2.98 |
| SD Alcohol 38B | 2.85 |
| Sylox 15x (thickening silica) | 2.00 |
| Cellulose Gum | 0.80 |
| Sodium Saccharin | 0.50 |
| Sodium Fluoride | 0.46 |
| Titanium Dioxide | 0.30 |
| Deionized Water | balance |

TABLE IV

Peroxide Gel Composition

| COMPONENT | WT. % |
|---|---|
| Carbopol 940 (2% solution) | 20.00 |
| Glycerin | 40.00 |
| Hydrogen Peroxide (35% food grade) | 12.00 |
| FD&C Blue | 0.005 |
| Sodium Hydroxide (50% soln) | adjusted to pH 7.0 |
| Deionized Water | Balance |

EXAMPLE 3

This Example illustrates a still further paste and gel combination for use in whitening teeth, the formulations being detailed under Table V and VI.

TABLE V

Bicarbonate Paste Composition

| INGREDIENT | WT. % |
|---|---|
| Polyol II (sorbitol and other sugars) | 33.90 |
| Calcium Carbonate | 27.00 |
| Sodium Bicarbonate | 20.00 |
| PEG 32 (polyethylene glycol) | 5.00 |
| Sodium Lauryl Sulfate | 3.00 |
| SD Alcohol 38B | 3.00 |
| Sodium Monofluorophosphate | 2.10 |
| Flavor | 1.00 |
| Cellulose Gum | 0.80 |
| Sodium Saccharin | 0.50 |
| Titanium Dioxide | 0.30 |
| Deionized Water | Balance |

TABLE VI

Peroxide Gel Composition

| COMPONENT | WT. % |
|---|---|
| Pluronic F127 | 25.00 |
| Glycerin | 25.00 |
| Hydrogen Peroxide (35% food grade) | 20.00 |
| PEG 1450 | 10.00 |
| Dipotassium Pyrophosphate | 0.750 |
| Disodium Pyrophosphate | 0.750 |
| FD&C Blue | 0.005 |

TABLE VI-continued

Peroxide Gel Composition

| COMPONENT | WT. % |
|---|---|
| Phosphoric Acid (85% w/w) | 0.10 |
| Deionized Water | Balance |

EXAMPLE 4

This Example illustrates a paste and gel combination incorporating urea peroxide for use in whitening teeth according to the method of the present invention, the formulations being detailed under Tables VI and VII.

TABLE VII

Bicarbonate Paste Composition

| INGREDIENT | WT. % |
|---|---|
| Sorbitol | 15.00 |
| Glycerin | 15.00 |
| Calcium Carbonate | 15.00 |
| Syloid 63XX (abrasive silica) | 15.00 |
| Sodium Bicarbonate | 15.00 |
| PEG 32 (polyethylene glycol) | 5.000 |
| Sylox 15x (thickening silica) | 3.60 |
| Sodium Lauryl Sulfate | 2.50 |
| SD Alcohol 38B | 2.50 |
| Sodium Hexametaphosphate | 2.00 |
| Flavor | 1.00 |
| Cellulose Gum | 0.80 |
| Sodium Saccharin | 0.50 |
| Sodium Fluoride | 0.46 |
| Titanium Dioxide | 0.30 |
| Deionized Water | Balance |

TABLE VIII

Peroxide Gel Composition

| COMPONENT | WT. % |
|---|---|
| Pluronic F127 | 25.000 |
| Glycerin | 35.000 |
| Urea Peroxide | 10.00 |
| Tetrapotassium Pyrophosphate | 4.00 |
| FD&C Blue | 0.005 |
| Phosphoric Acid (85% w/w) | 0.10 |
| Deionized Water | Balance |

EXAMPLE 5

The following Example illustrates the whitening effectiveness of a hydrogen peroxide and sodium bicarbonate combination wherein each of these active components have been stored separate just prior to use. Ordinarily, the peroxide and bicarbonate are combined within ten minutes, preferably five minutes but optimally within two minutes of their mixing (onto the teeth).

The test utilized the paste and gel components whose formulations are detailed under Tables IX and X.

TABLE IX

Bicarbonate Paste Composition

| INGREDIENT | WT. % |
|---|---|
| Polyol II (sorbitol and other sugars) | 33.60 |
| Syloid 63XX (abrasive silica) | 30.00 |
| Sodium Bicarbonate | 10.00 |
| PEG 32 (polyethylene glycol) | 5.00 |
| Sylox 15x (thickening silica) | 2.00 |
| Flavor | 1.00 |
| Sodium Lauryl Sulfate | 2.98 |
| SD Alcohol 38B | 2.84 |
| Cellulose Gum | 0.80 |
| Sodium Saccharin | 0.54 |
| Menthol | 0.50 |
| Sodium Fluoride | 0.44 |
| Titanium Dioxide | 0.30 |
| Deionized Water | Balance |

TABLE X

Peroxide Gel Composition

| COMPONENT | WT. % |
|---|---|
| Glycerin | 40.00 |
| Pluronic F127 | 22.00 |
| Hydrogen Peroxide (35% food grade) | 17.14 |
| Zinc Citrate Trihydrate | 4.00 |
| FD&C Blue | 0.005 |
| Phosphoric Acid (85% w/w) | 0.15 |
| Deionized Water | Balance |

Evaluation of whitening involved placing a tooth into the sampled composition for the equivalent of two minutes per day exposure (i.e. one week is equivalent to 14 minutes exposure). Subsequently the test tooth was evaluated for whiteness on a Macbeth Colorimeter. A Delta L value was recorded representing the difference between the calorimeter reading of the tooth baseline versus the value after exposure to the sampled composition. Where the gel composition was used as a test substrate, the concentration of hydrogen peroxide delivered was maintained at 3.0% active hydrogen peroxide.

TABLE XI

| | Equivalent Use Time (in Months) | | | |
|---|---|---|---|---|
| | 0 | One | Two | Three |
| | | Delta L Values | | |
| Bicarbonate Phase | 0 | 1 | 3 | 4 |
| Gel Phase | 0 | 8 | 18 | 21 |
| Gel/Bicarb. Phase Combination | 0 | 20 | 29 | 30 |

Values in Table XI are recorded as Delta L values. The higher the Delta L value the more effective the whitening. The results indicate that combination of gel/bicarbonate phase provided a substantially greater whitening effect than the additive results of the gel and bicarbonate phases separately. For instance, at the equivalent use time of one month, the additive of a bicarbonate and gel phase provides a Delta L value of 9. By contrast, combination treatment with gel/bicarbonate phase results in a whitening with Delta L value of 20.

EXAMPLE 6

The following Example demonstrates the effect of pH on whitening performance. Compositions employed for these experiments were essentially identical to those described under Table IX and X of Example 5. The only differences were that the level of hydrogen peroxide was varied as well as pH (by addition of appropriate amounts sodium hydroxide or sodium carbonate). Table XII records the Delta L values for one month of brushing.

TABLE XII

| HYDROGEN PEROXIDE LEVEL (% DELIVERED) | pH | DELTA L VALUE |
|---|---|---|
| 0.75 | 7.9 | 13 |
| 1.5 | 8.2 | 19 |
| 0.75 | 9.5 | 24 |
| 1.5 | 9.5 | 26 |
| 1.5 | 10.5 | 32 |

From the results listed in Table XII, it is evident that for any given level of peroxide, the higher the pH the greater the whitening performance.

The foregoing description and Examples illustrate selected embodiments of the present invention and in light thereof various modifications will be suggested to one skilled in the art, all of which are within the spirit and purview of this invention.

What is claimed is:

1. A method for whitening teeth comprising:
   (i) providing an oral composition which includes a first and second composition each of which is stored separate from one another prior to time of use, the first composition containing from 0.01 to 20% of a peroxide by weight of the oral composition, and the second composition containing from 0.05 to 60% of a bicarbonate salt by weight of the oral composition, and the oral composition having a pH from 9.0 to 12;
   (ii) dispensing the first and second compositions onto a toothbrush;
   (iii) applying the first and second compositions from the toothbrush to the teeth:
   (iv) brushing the teeth thereby mixing first and second compositions together; and
   (v) repeating steps (ii) through (iv) on a plurality of days, the teeth to be whitened being exposed to the oral composition for the equivalent of 10 seconds to 5 minutes per day exposure until the delta L values of the equivalent use time of combined peroxide and bicarbonate compositions provide substantially greater whitening effect than additive results of tooth whitening with either peroxide or bicarbonate compositions used separately, as represented by differences between colorimeter readings of tooth base line versus values after exposure.

2. The method according to claim 1 wherein each of the first and second compositions are semi-solids.

3. The method according to claim 1 wherein the peroxide is hydrogen peroxide.

4. The method according to claim 3 wherein hydrogen peroxide is present in an amount from 0.5 to 10% by weight of the oral composition.

5. The method according to claim 1 wherein sodium bicarbonate is present in an amount from 0.05 to 40%.

6. The method according to claim 1 wherein the oral composition is dispensed from a dispensing container in pump form.

7. The method according to claim 6 wherein the dispensing container has an upper and a lower body which are telescopically engageable one with another, the upper body including at least two hollow and separate parallel cylinders, the cylinders having a first generally closed end and a second end telescopically and slidingly accommodating at least two parallel pistons which conform to ride sealingly along the interior walls of the cylinders so as to force any flowable materials to flow toward the first end of the cylinder upon relative compression of the cylinders and pistons, the cylinders having outlet channels;

an outlet means in fluid communication with the outlet channels, the outlet means including adjacent outlet openings unconnected to each other and having means for causing the flowable materials to flow toward each other at the outlet openings to form a banded, unmixed stream;

the first and second compositions being the flowable materials and stored in separate ones of the at least two hollow parallel cylinders; and the method further comprising the step of actuating the dispenser container to dispense the unmixed stream.

8. The method according to claim 7 wherein the unmixed stream is placed upon a toothbrush and applied to the teeth, and mixing is performed in the mouth so as to whiten the teeth.

* * * * *